United States Patent [19]

Mazurek

[11] Patent Number: 5,457,050
[45] Date of Patent: Oct. 10, 1995

[54] AGAROSE PLUG MOLD AND PROCESSING CHAMBER

[75] Inventor: Gerald H. Mazurek, Tyler, Tex.

[73] Assignee: Board of Regents, The University of Texas System, Austin, Tex.

[21] Appl. No.: 160,103

[22] Filed: Nov. 30, 1993

[51] Int. Cl.[6] ............................ C12J 3/20; B28B 15/00; B29C 33/46; B41B 11/54
[52] U.S. Cl. ............................ 435/270; 935/85; 425/89; 249/141; 249/160; 249/168
[58] Field of Search ............................ 435/270; 935/85; 425/89; 249/141, 160, 168

[56] References Cited

U.S. PATENT DOCUMENTS 4,944,483  7/1990  Nishizawa .................................. 249/83

OTHER PUBLICATIONS

Arbeit et al., "Resolution of Recent Evolutionary Divergence among *Escherichia coli* from Related Lineages: The Application of Pulsed Field Electrophoresis to Molecular Epidemiology," *The Journal of Infectious Diseases*, 161:230–235, 1990.
Hector et al., "Large Restriction Fragment Patterns of Genomic *Mycobacterium fortuitum* DNA as Strain-Specific Markers and Their Use in Epidemiologic Investigation of Four Nosocomial Outbreaks," *Journal of Clinical Microbiology*, 30(5):1250–1255 (Aug., 1992).
Mazurek et al., "Large DNA Restriction Fragment Polymorphism in the *Mycobacterium avium–M, intracellulare* Complex: a Potential Epidemiologic Tool," *Journal of Clinical Microbiology*, 31(2):390–394, 1993.
Patterson et al., "Epidemiology of an Endemic Strain of S-Lactamase-Producing *Enterococcus faecalis*," Journal of Clinical Microbiology, 29(11):2513–2516, 1991.
Zhang et al., "DNA Polymorphisms in Strains of *Mycobacterium tuberculosis* Analyzed by Pulsed-Field Gel Electrophoresis: a Tool for Epidemiology," *Journal of Clinical Microbiology*, 30(6):1551–1556, 1992.
Birren and Lai, "Pulsed Field Gel Electrophoresis: A Practical Guide," *Academic Press, Inc.*, 1993, pp. 27–31.
Schwartz, D. and Cantor, C. "Separation of Yeast Chromosomes Sized DNA by Pulsed Field Gradient Gel Electrophoresis", *Cell* vol. 37 pp. 67–75 (1984).

Primary Examiner—Michael G. Wityshyn
Assistant Examiner—T. J. Reardon
Attorney, Agent, or Firm—Arnold, White & Durkee

[57] ABSTRACT

An apparatus and method for the preparation of large DNA molecules from cells which have been cast in agarose. Specifically, the invention provides for a processing chamber that allows agarose plugs to be molded and processed within the same apparatus. This greatly reduces the amount of manipulation required of such DNA samples and reduces the loss of material due to agarose plug breakage. The mold has a filling port for agarose and a slot for at least one retainer for preventing the molten agarose from exiting through openings in the mold through which DNA processing solutions later access the molded agarose plugs.

12 Claims, 3 Drawing Sheets

AGAROSE PLUG MOLD AND PROCESSING CHAMBER

BACKGROUND OF THE INVENTION

A. Field of the Invention

This application deals generally with an apparatus and methods for the preparation of large DNA fragments in agarose plugs.

B. Description of the Related Art

Methods for preparing large DNA fragments in agarose are well known to those of skill in the field of molecular biology. With care, conventional methods allow molecules as large as 500 kD ("Kilo Daltons") to be prepared. However, the common steps in handling DNA, that is, pipetting and phenol extraction, introduce shear forces that reduce the length of DNA. Therefore, mechanical breakage due to handling procedures is a major hindrance to the preparation of large DNA. Once prepared, large DNA requires gentle handling but is relatively stable, particularly if the DNA is maintained at high concentrations.

To prepare DNA larger than 500 kb, it is necessary to protect the molecules from both mechanical breakage and nucleolytic degradation during the entire isolation process. Schwartz and Cantor prepared chromosomes from yeast by embedding the cells in agarose prior to solubilization and enzymatic digestion of the non-DNA components. The same general procedures originally developed for yeast chromosomes have been adapted for preparing large DNA from all other sources. In general, the typical steps in DNA preparation in this manner are as follows.

Cells to be embedded in agarose for DNA isolation can come from either unicellular organisms, multicellular tissues, or blood. Prior to being embedded in agarose, single cell suspensions must be obtained. For example, tissues must be dissociated, white blood cells must be concentrated, and cultured unicellular organisms must be harvested. The single cell suspensions are usually washed, and then, since the final DNA concentration can be critical, the cell number must be determined prior to embedding. Individual cells are embedded in agarose, which protects the DNA against breakage while allowing the free flow of solutions necessary for lysis and digestion. The samples are typically maintained in detergent and high concentrations of EDTA to inhibit nuclease activity. Proteinase K is fully active in such solutions (as are some other proteases, such as pronase) and therefore will digest cellular protein under conditions during which any endogenous enzymes are unable to modify or degrade the DNA. Material released by this digestion diffuses out of the agarose during the washes while the DNA remains trapped. Because cellular enzymes are removed completely by this procedure, samples prepared in this way are extremely stable and show little degradation during storage periods as long as several years.

Organisms that contain a cell wall often require an additional step specifically designed to disrupt the wall prior to proteinase K digestion to allow the lysis solution access to the membrane. This procedure will allow the lysis solution access to the membrane. This procedure usually will another enzymatic step, for example, digestion of fungal cell walls to form spheroplasts, although in other cases mechanical force can be used, as for vascular plants.

DNA prepared in agarose remains available as a substrate for all the common enzymatic steps of molecular biology. Restriction enzymes recognize and cleave their target sites in embedded DNA. Additionally, other endo- and exonucleases can be used for labeling and ligation. If enzymatic steps are required for DNA prepared in agarose, it is essential to use agarose that is free of material that would inhibit these enzymes. The relative purity of different lots of agarose varies, as does the sensitivity of different enzymes to the contaminating compounds. Users should either pretest lots of agarose for compatibility with in-gel uses (using the intended enzymes) or use a commercially available agarose certified for its suitability for this purpose (e.g., InCert Agarose, FMC BioProducts). Although such agarose is expensive on a per gram basis, only small amounts are used in normal plug preparations. These expensive types of agarose are not necessary or helpful when preparing samples such as yeast chromosomes for size markers when no restriction digestion is required.

Once DNA is prepared in agarose the concentration cannot be changed. DNA samples can be prepared either in solid agarose, which then can be transferred as individual blocks, or in agarose microbeads, which can be pipetted. Each technique permits different amounts of the sample to be digested or run on a gel. Some prefer to prepare samples in solid agarose blocks, finding it more amenable to the simultaneous production of multiple samples and the exchanging of buffers prior to digestion. For procedures that are extremely sensitive to residual reagents, the greater surface area of microbeads permits more extensive dialysis, although loss of DNA from the surfaces of the beads lowers the yield.

As agarose embedment has become more accepted in the art, various apparatus for molding agarose plugs have been developed. Early sample molds allowed formation of one plug at a time, which was tedious and required different molds to prepare samples of different thicknesses. Two alternative molds for preparing solid samples in batches having long shallow channels (whose width and depth correspond to the dimensions of the sample comb) milled in acrylic blocks were then developed. The open side of each groove is covered with tape, and agarose-DNA mixture is pipetted in from one end. After the agarose solidifies, the long ribbon of sample is cut to convenient lengths before being subject to enzymatic treatment.

It is possible to prepare samples in square acrylic tubing by taping one end closed prior to pipetting in the agarose-DNA mixture. The tube can be placed in ice for rapid hardening; the long square "noodle" slips out of the tube easily after removal of the tape. Samples can be digested and washed intact. Samples similarly can be formed in TYGON tubing, 1-ml syringes with the front end cut off, plastic drinking straws, or glass pipets. Using round samples results in slightly more DNA migrating in the center of each lane than near the edges. Individual samples of constant thickness are sliced from the ends using a template. Major benefits of this "noodle" method are that uniformly sized samples can be prepared rapidly with large volumes of sample and, by using slicing templates with gaps of different widths, samples can be sliced accurately to different thicknesses. This variability permits different amounts of DNA to be handled in blocks of similar height and width for greater uniformity in digestion and electrophoresis.

Unfortunately, previously described devices have required that plugs be cast, and then processed in a separate device. These methods for preparing and embedding cells in agarose involved the movement of the individual plugs from solution to solution, this occurs about ten times during the development of each plug. Agarose plugs are very fragile, and breakage can occur during the transfer process. Given the fragile nature of large DNA molecules and the agarose plugs in which they are prepared, a device that would allow cells to be embedded in agarose and then processed in the same device would greatly reduce the manipulation and therefore degradation of large DNA molecules.

SUMMARY OF THE INVENTION

Several of the deficiencies of the past methods and apparatus for casting and processing agarose plug molds are remedied by the present invention. This invention allows plugs to be cast and processed in the same device, therefore resulting in much less manipulation of the plugs. Specifically, the invention involves a disposable apparatus comprising a mold, which forms the plugs and protects them during processing, and removable retainer sheets.

As an initial point, following patent law convention, the use of the article "a" or "an" in front of a word or phrase in the specification, including the claims, denotes that one or more of the described components is present in a particular embodiment of the invention.

In a general embodiment, the invention contemplates an apparatus adaptable for casting and processing cell-containing agarose plugs. A major aspect of the invention is that the agarose plugs are cast and processed within a mold which is designed to both form the agarose plugs and then contain the plugs as the plugs are transferred from solution to solution during the DNA isolation process. Typically, the apparatus will involve a mold. The mold will define a chamber to which a molten agarose/cell mixture is placed. After the agarose has solidified, the mold performs a protective function by containing and protecting the fragile agarose plugs during the development process. The mold itself typically has a filling port which allows the molten agarose cell mixture to be poured into the mold, and an opening through which solutions necessary to process the cells to obtain substantially pure DNA can access the plugs. The apparatus typically comprises a retainer which is able to prevent molten agarose from exiting the mold until it solidifies. In an embodiment of the invention, this retainer is designed so that it can be removed after the agarose has solidified.

In a first embodiment of the invention, the mold comprises separate halves which connect together to form a complete mold. Typically, the two halves will be substantially identical, thereby reducing the need to produce more than one component. The two halves of the mold may be connected together prior to filling the mold with molten agarose. In an embodiment of the invention, the two halves are connected by a connector projection/connector projection receiving hole system which is integrally formed in the halves. Of course, the halves may be connected in any number of manners, including, for example, being taped or clipped together. Further, it is possible to have the halves connected along a foldable hinge line such that one piece of material is folded upon itself and connected to form the mold.

The retainer of the apparatus is typically a sheet retainer. In certain embodiments, the sheet retainer is adapted to pass through a slit in the side of the processing mold and define an agarose molding space, or spaces, within the chamber defined by the mold. In a typical example of the invention, two or more sheet retainers are passed through each processing mold. The retainers block holes through the mold during the agarose solidification process. The holes in the mold are designed for passage into the mold chamber of solutions necessary to process DNA once the agarose has solidified and the DNA preparation has begun. Typically, a number "n" of plastic retainers will define "n-1" molding spaces within the mold chamber. This is because the retainers which lie against the inner surface of the panels and block the panel holes will not have agarose on the side proximal to the inner surface of the panel, whereas the other retainers will have agarose on both sides of them. After the agarose is solidified, the sheet retainers of preferred embodiments are removable. Removal of the retainers results in "n-1" plugs being left in the mold. The plugs may be partially attached to each other by agarose solidified in the filling port(s) of the mold.

Another embodiment of the present invention is drawn to a plug mold and processing apparatus which has two halves, each half having a panel, a side extending from the panel and an end extending from the panel. The panels have openings for the passage of processing fluids into and out of a chamber defined by the panels, side and the end of the halves. The sides of the apparatus have a slot for a retainer that is capable of preventing molten agarose from flowing out of the chamber through the processing fluid passages. The end of a half has a filling port which allows for filling the assembled mold with molten agarose. The two halves are joined together by a connector.

The present invention also contemplates the use of the apparatus of the above-described apparatus for preparing relatively pure DNA from cells. This method involves obtaining cells, and preparing them in the manner necessary. The prepared cells are then mixed with molten agarose, and the agarose/cell mixture is introduced into the above-described apparatus. The molten agarose is allowed to solidify, and the resulting agarose/cell plugs are then processed to obtain relatively pure DNA from the cells.

A better appreciation of the present invention may be obtained by viewing the figures and by reading the detailed description of the preferred embodiments of this application.

DETAILED DESCRIPTION

Figure 1:
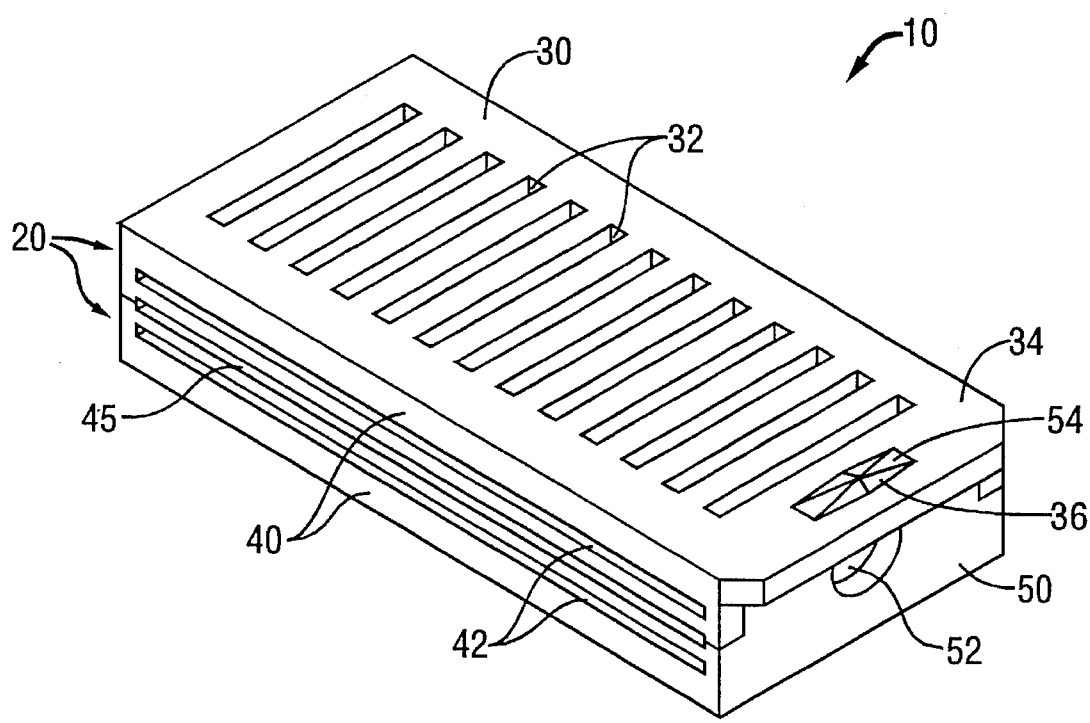
FIG. 1: An isometric view of one embodiment of the plug molding apparatus of the present invention.
Figure 2:
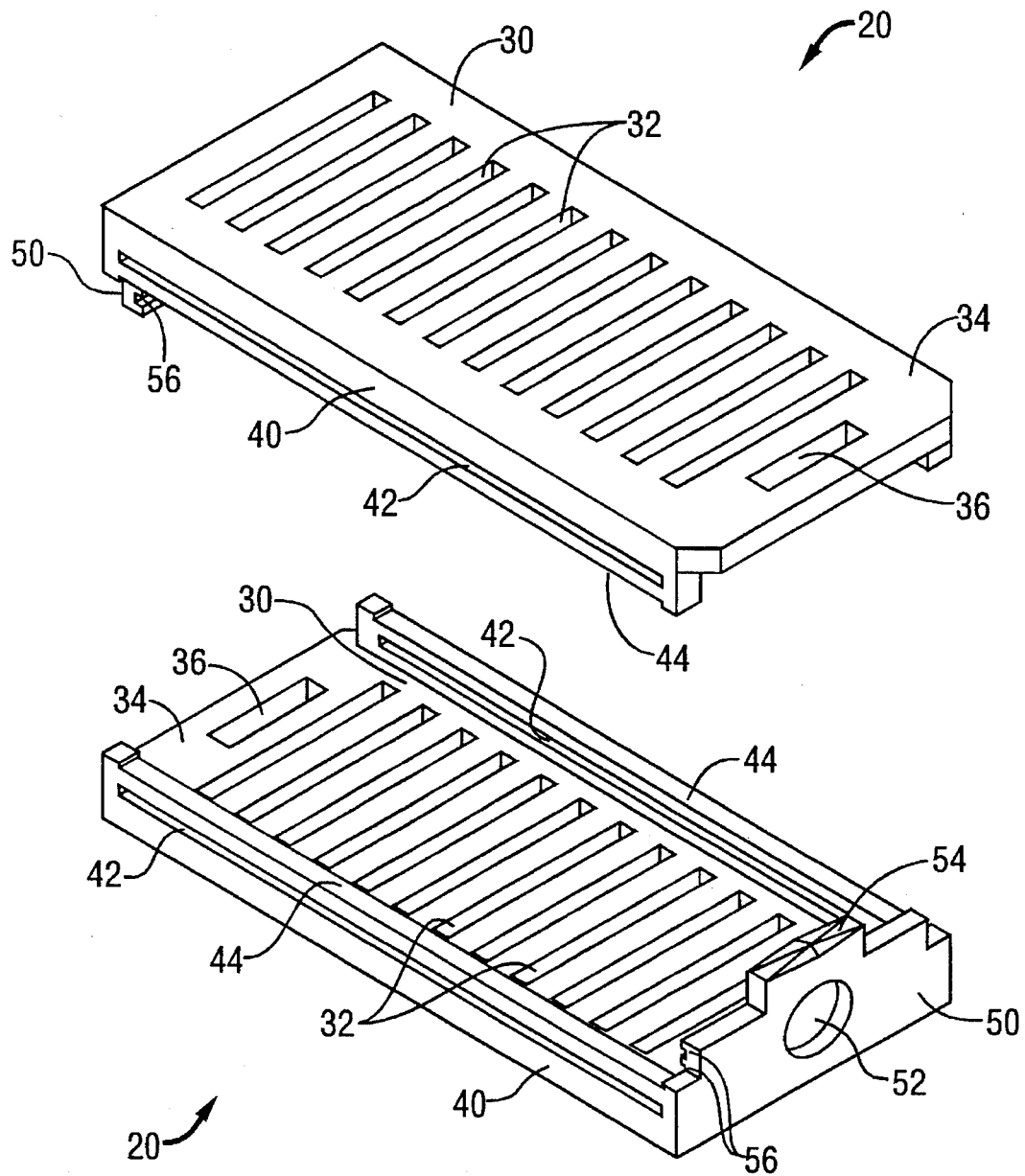
FIG. 2: An isometric exploded view of one embodiment of the plug molding apparatus of the present invention.
Figure 3:
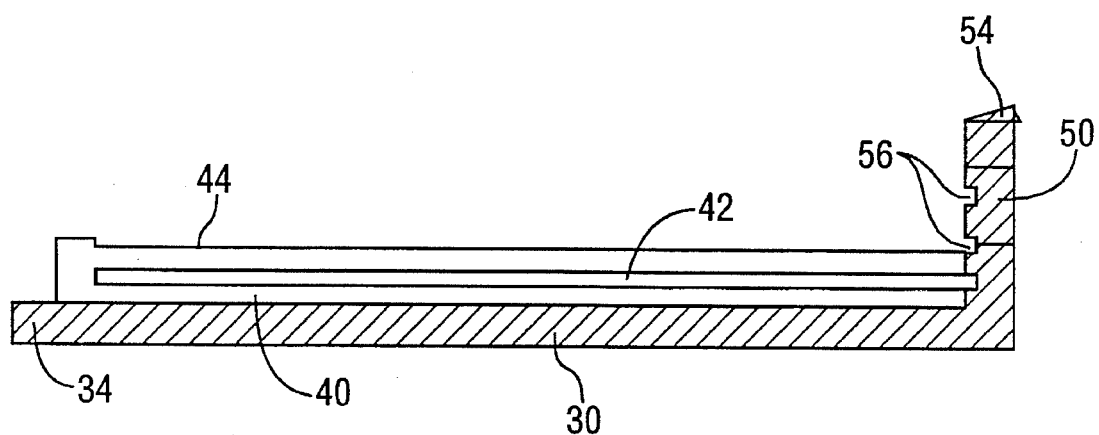
FIG. 3: A side view of one half of the plug molding apparatus of the present invention.

For the purpose of illustration, but not limitation, the following embodiments of this invention are described. Of course, those of skill in the art will understand that there are many variations which can be made in these embodiments which would still be within the scope and spirit of the present disclosure.

EXAMPLE I

Processing Chamber

One embodiment of the present invention is illustrated in FIGS. 1–4. Plug mold 10 is formed of mold halves 20. The halves are substantially identical and are designed such that two substantially identical halves snap together to define a chamber. A single half 20 has a panel 30, two sides 40, and an end 50. Each of these has a chamber interior surface and a chamber exterior surface.

Mold halves 20 are typically formed out of plastic. Usually, a relatively hard plastic such as polyethylene is used to make the apparatus. However, any form of plastic or other material which can withstand the temperature of the melted agarose and contain the agarose until solidification may be used to make the mold. Further, the mold should be able to withstand any chemicals which are employed in the processing steps of the isolation procedure. Of course, materials such as metal, rubber, fiberglass, or wood could be employed to make the mold. It is anticipated that the molds will be disposable, since it is possible to make them out of a relatively inexpensive material, and washing them will probably not be economically feasible. Of course, it is possible that for some specialty applications, specific, more expensive, materials may need to be used. Of course, any of the molds, may be washed and reused if desired.

Typical dimensions of the assembled plug mold are 20–30 mm long, 10–15 mm wide, and 5–8 mm thick. The dimensions may vary, based upon the size of the agarose plugs desired. The thickness of the chamber will vary based upon the number of retainers 60 to be employed in a particular chamber. The number of retainers in a mold defines the number of agarose plugs which a particular mold is designed to cast. A typical agarose plug is approximately 20 mm long, 9 mm wide, and 1 mm thick. However, these dimensions are not limiting, and plugs of almost any conceivable size may be created by varying the dimensions of the mold and retainers appropriately.

Panel 30 includes passages 32. Passages 32 allow for solution to flow into and out of the chamber. Although this embodiment of the invention has passages, the invention can be practiced without the presence of passages 32 in the panel. Further, the passages 32 need not be slit-shaped as in this embodiment. Any passage shape that will allow fluid to flow into and out of the chamber, while preventing the agarose plugs from exiting the chamber may be employed in the invention. Therefore, the slit-shaped passages 32 could be replaced with, for example, square, round or irregularly shaped holes without deviating from the spirit of the invention. Panel 30 has connector tab 34 extending from panel 30 distal in a direction away from end 50. Connector tab 34 has hole 36 in it. Hole 36 is designed to receive connector projection 54, which extends from end 50 of half 20. When two halves 20 are assembled to form plug mold 10, hole 36 of one half 20 receives connector projection 54 of the other half 20, and vice versa. Thereby securing the halves together and forming a complete plug mold. While this connector system is used in the present embodiment, one could easily employ other connectors without deviating from the spirit of the invention. For example, two halves may simply be taped together, clips for connecting halves together may be provided, plug and hole type connectors could be used, etc.

Side 40 of half 20 projects from the chamber interior surface of panel 30. Side 40 runs the length of panel 30, from end 50 to connector tab 34. Side 40 has slot 42 for receiving retainer sheet 60. Slot 42 runs substantially the length of side 40. Sides 40 also have half slot 44 for receiving retainer sheet 60. Half slot 44 is designed so that when halves 20 are assembled to form plug mold 10, a medial slot 45 is formed at the juncture of the two halves by half slots 44 of each half 20. Medial slot 45 has approximately the same dimensions as slot 42. One of skill in the art will appreciate that, although the present embodiment has a total of three slots when assembled, any number of slots may be employed in the present invention. If two slots are employed, only a single agarose plug will be created in the chamber, as the plug will be created in the space between the two retainers.

The third slot, such as medial slot 45 is added and then fitted with a third retainer, two agarose plugs will be formed within the chamber. If five slots occur in the chamber, four agarose plugs can be cast in the same chamber.

End 50 of half 20 has filling port 52. Filling port 52 allows for molten agarose to be poured into the assembled chamber. In the pictured embodiment, filling port 52 is circular. However, the filling port may be almost any shape, including square or rectangular. Filling ports which are not circular may enjoy certain advantages over circular filling ports in cases where a relatively large number of retainer sheets are used. The retainer sheets 60 define spaces in which agarose plugs are formed, and it is desirable to completely fill each such space in order to obtain a maximum number of usable agarose plugs from each chamber. If a circular filling port 52 is used in conjunction with a large number of retainer sheets, the circular configuration of the port may make it more difficult to fill the spaces between more peripheral retainer sheets. Therefore, a square or rectangular filling port 52 can allow greater access to spaces between peripheral retainer sheets.

End 50 also has connector projection 54 projecting away from the juncture of end 50 with panel 30. As previously described, connector projection 54 is designed so as to fit within hole 36 of a mating half 20, thereby connecting two halves 20 to form assembled plug mold 10.

End 50 also has channels 56 for receiving edges of retainer sheets 60. These channels are formed into the interior face of end 50. Channels 56 are positioned such that they form a continuation of the passages formed by slots 42 and 45 when the chamber is assembled.

Retainer sheets 60 are dimensioned so that they slide within the passages formed by slots 42 and 45 and channel 56. Sets of retainer 60 define spaces into which the molten agarose is poured prior to solidifying into plugs. Each such space defines the boundaries of a single agarose plug. Retainer sheets 60 are typically made from a somewhat flexible plastic material. Retainer sheets 60 are typically about 0.05–1.0 mm thick with 0.1 mm being a typical average thickness. However, other thicknesses could also be acceptable. Since retainer sheets 60 are designed to slide out of the processing chamber once the agar has solidified, they should have a surface which will allow for sliding against the plugs without unduly disrupting the relatively fragile agarose plugs. Therefore, relatively slick plastic is typically used. Of course, it is possible to have a slippery coating, such as Teflon™ or silicone spread upon the retainer sheets 60 to facilitate the slipping of the retainers out of the chamber. Further, it is not necessary that the retainers be made of plastic. For example, retainers made of cardboard, especially cardboard with a plasticized, glazed, or laminated surface, or metal may be employed in the invention. Those of skill in the art will recognize that there may be other forms of retainers which may be used without deviating from the spirit or scope of the invention.

Figure 4:
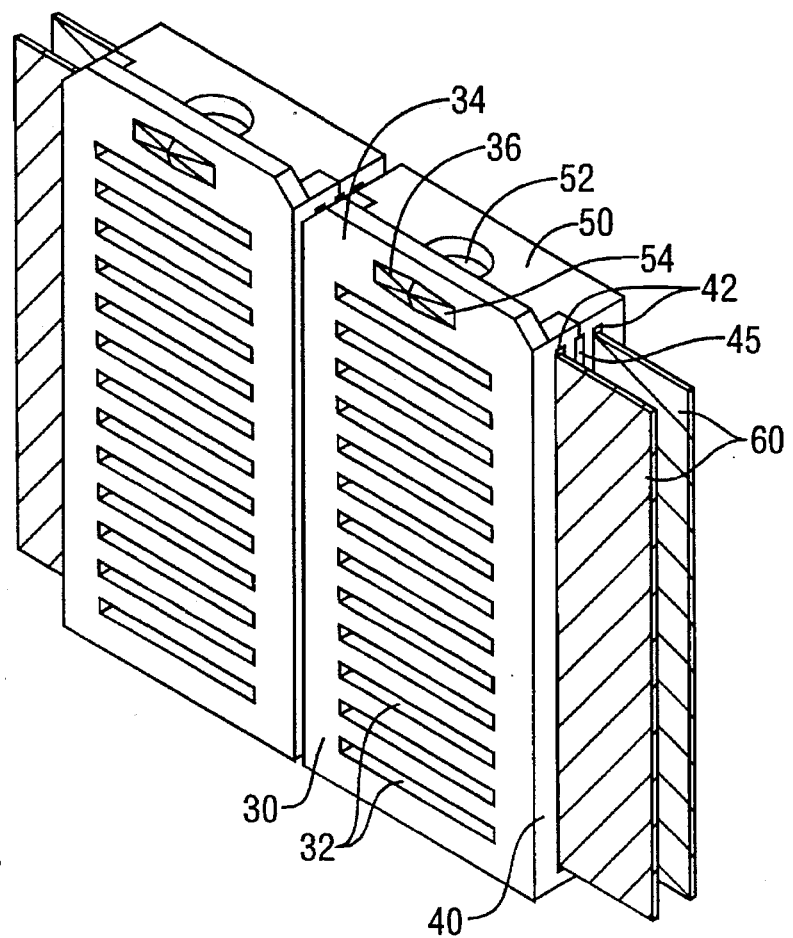
FIG. 4: An isometric view of the plug molding apparatus of the present invention in position for the introduction of agarose into the mold.

The invention is designed such that multiple chambers 10 may be strung along a single set of retainers 60. This is shown in FIG. 4. A group of chambers 10 that have been positioned on a single set of retainers 60 may, after the agarose has hardened, be easily slid into a beaker for processing.

EXAMPLE II

Use of Agarose Plug Mold Processing Chamber

Typical use of the chamber to cast and process agarose plug molds is as follows. Halves 20 are joined together to form assembled plug mold 10. As many molds as desired are assembled in this manner. An appropriate number of retainers 60 are threaded through the passage defined by the slots 42 and 45 and channel 56 of the molds. More than one chamber can be strung upon a single set of retainers if desired, as illustrated in FIG. 4. The filling port of one end of the assembled mold is plugged. This end will be in a downward position when the mold is filled through the filling port of the other end of the mold. The filling port is typically plugged by simply taping over it. However, a plug or any other means of filling the port may be employed. It is also possible to produce non-identical halves, and place a filling port in only one half. This would eliminate the need for plugging the filling port of the downward end of the mold, however, it would result in the need for two non-identical halves to assemble the mold.

After the mold apparatus has been assembled, cells of the organism from which DNA is to be isolated are prepared as is typical in the art. Those of skill in the art will know how to prepare cells from various sources. For example, cells from multicellular animals may have to be disrupted prior to casting of the plugs. The prepared cells are typically pelleted by centrifugation, and then washed with tris-EDTA buffer ("TE"). The formula for TE buffer is as follows: Tris-Hcl 10 mM and EDTA 1.0 mM. The cells are then resuspended in TE to a desired concentration. Concentration may be measured in McFarland units, a measure of optical density. Typically, the cells are resuspended to an optical density of 1–4 McFarland units. However, almost any concentration of resuspended cells can be employed in the invention, so long as the number of cells used contain sufficient DNA to make the isolation worthwhile, and a number of cells so large that it disrupts the solidification of the agarose is not used.

The resuspended cells are mixed with an approximately equal volume of melted low melting point agarose. There are multiple grades of agarose which may be employed in producing agarose plugs for DNA production. Agarose grade is based on purity, the amount of sulfate in the agarose mixture, and the number of sulfide bonds which the agarose forms. Typically a high purity, low melting point agarose is used for DNA production. One of the best grades of agarose for use in the invention goes by the name of InCert™. A drawback to InCert™ agarose is expense. Therefore, the inventors typically use electrophoresis GTG grade, agarose from a company such as FMC. Of course, those of skill in the art will understand that varying grades of agarose may be used, so long as impurities in the agarose do not contaminate the prepared DNA and that the gelled agarose is not too fragile. One advantage of the present invention is that a lower concentration of agarose may be employed in the invention, since the processing chamber will protect agarose during the preparation of the DNA. The less agarose in a gel, the less dense and the more fragile the gel. However, the ability to lower the concentration of agarose in the gel has several advantages. Enzymes used in developing the DNA can more rapidly defuse into and out of less dense gels. Therefore, by protecting the fragile gel, the present processing chamber allows lower amounts of agarose to be used, and can result in more rapid production of DNA.

Agarose melts at around 58° C., however, unlike a true solid agarose does not solidify at the same temperature at which it melts. Rather it solidifies at a lower temperature. The cells are typically mixed with the agarose at around 50° C. However, there is a large range of temperatures at which the agarose can be poured. Typically, agarose solidifies at around 35° C. Therefore, if the temperature of the agarose is less than around 37° or 36° at pouring, the agarose tends to solidify rapidly and this causes problems in filling the chamber. The upper limit of temperature on the agarose is typically the temperature at which DNA tends to denature. Short pieces of DNA tend to denature at around 70° C. and normal denaturization temperatures for DNA in scientific protocols are about 90° C. Therefore, one will typically not wish to mix cells with agarose which is warmer than 70° C. However, for certain protocols it is possible that it may be desirable to denature the DNA prior to casting of the plugs, and in this case the temperature of the agarose can be controlled so that denaturization does occur.

After the cells and agarose are mixed at an appropriate temperature, the molten agarose/cell suspension is injected into the filling ports at the end of the processing chamber and allowed to solidify by cooling. Care should be taken during the filling process to make certain that all of the spaces between the retainers are filled, so that a maximum number of complete plugs will be made. The plugs are then allowed to solidify by cooling. Cooling may be hastened by placing the molds at a reduced temperature such as on ice or in a refrigerator.

After the plugs have solidified, the chambers containing the solidified plugs are removed from the retainers. This is accomplished by simply sliding the plugs off of the retainers. The chambers are then placed in a container, typically a beaker of appropriate size. The placement of the molds in the container allows agarose plugs to be bathed in the appropriate solutions during DNA isolation. The molds protect the fragile plugs during this process. Therefore, the plugs need not be treated as carefully as they would have to be if they were not contained in a mold. The solutions and washes of the plugs in the process may be changed by simply pouring the old solution out of the breaker and pouring the new solution in. Next, the chambers are covered with a solution which breaks down the cell wall of the cells, thereby lysing the cells. Typically, the cell walls are broken down with a solution of lysozyme and β-mercaptoethanol. However, the particular enzyme used to break down the cell walls is somewhat organism dependent, and those having ordinary skill in the art will be able to determine which enzymes may be most appropriate for the types of cells from which the DNA is being isolated. For example, certain advantages may be realized in using zymalase, neuraminidase, etc. Further, the inventors have found that it is not necessary to include β-mercaptoethanol, which may increase the activity of the enzymes by relaxing disulfide bonds, in order to obtain cell wall breakdown. The advantage of leaving β-mercaptoethanol out of the mixture is that β-mercaptoethanol has a smell which is considered unpleasant by many. The inventors have typically used a solution comprising TE buffer containing 1 mg/ml lysozyme in TE buffer to lyse the bacterial cell walls.

The cells are typically incubated in the cell wall lysing solution for approximately four hours. However, this time period can be varied according to the specific protocol or the desires of the person isolating the DNA, and the four hour time period is in no way critical. A lower limit on the time level is set by the amount of time necessary to lyse the cell wall, which will be readily determinable by those of skill in the art. The upper limit on time of incubation is dictated mainly by convenience. For example, the plugs may be incubated in the cell wall lysing solution overnight without adverse affects. Typically, the plugs may be placed on a shaker at approximately 37° C. during incubation. Obviously, it is preferable to maintain the temperature of the plugs and cell lysing solution at a point somewhere around the optimum functioning temperature of the enzyme being employed to lyse the cell wall. With lysozyme, this is approximately 37°.

After the cell walls have been lysed, the chambers are removed from the lysing solution. This can be done simply by pouring the solution out of the container in which the plug molding chambers are contained. It may be desirable to perform one or more washes with TE buffer to remove any last vestiges of the lysing solution prior to moving on to the next step.

Next, the agarose plug containing molds are transferred to a solution which is designed to destroy any DNAse and break down the cell membranes. Typically, proteinase K or a similar proteinase is used in this process, along with SDS or another detergent such as sarcosine. The proteinase and detergent solution is typically based on TE buffer. The plugs may be incubated in 1% SDS and 1 mg/ml proteinase K in TE buffer. Typically, the plugs are incubated for 8–16 hours at approximately 55° C. The 8–16 hour period can be varied depending on the organism. If desired, the plugs may be stored in this solution for an indefinite amount of time. Further, the incubation temperature may vary. The inventors have found that incubation works best at 50°–55° C., and that higher temperature may cause melting of the agarose plugs.

After the proteinase incubation is completed, the agarose plug containing chambers are washed. Typically, TE buffer is used for the wash, as it is used as the basis for all of the solutions in the DNA production process. However, those of skill in the art will recognize that many different buffers can perform the same function as the TE buffer, and the invention is not limited to the use of TE buffer. Washing may be accomplished by placing the plug containing molds into TE buffer for 30 minutes, and then repeating the washing step several times. The plugs may be washed approximately five to six times. Further, the later washes may take longer than the initial ones due to a relatively smaller amount of material being removed in each of the later washes.

Once the washing step is completed, the agarose plugs contain relatively purified DNA. Typically, the molds are opened to release the agarose plugs, which are then stored in TE buffer for later use. Small plastic vials containing TE may be used to store the agarose plugs. The plugs may also be stored in the plug molds. Individual plugs formed between multiple retainers within a single chamber will typically separate upon opening the chamber. The individual plugs may be joined together by small pieces of solidified agarose which formed in the filling ports. However, agarose is fairly fragile and these connections should break upon opening the vial. If the connections do not break, the plugs may be pulled apart or cut apart.

The pure DNA contained in the agarose plugs may be digested with various restriction enzymes, loaded onto gel electrophoresis equipment, used for polymerase chain reactions, ligating, or used in any number of protocols known to those of skill in the art.

REFERENCES

The pertinent portions of the following references are incorporated by reference in this application.

1. Jan Evans Patterson et al., "Epidemiology of an Endemic Strain of β-Lactamase-Producing *Enterococcus faecalis*", *J. or Clinical Micro.*, 29(11):2513–2516 (Nov. 1991).
2. Janel S. R. Hector et al., "Large Restriction Fragment Patterns of Genomic *Mycobacterium fortuitum* DNA as Strain-Specific Markers and Their Use in Epidemiologic Investigation of Four Nosocomial Outbreaks", *J. of Clinical Micro.*, 30(5):1250–1255 (May 1992).
3. Yansheng Zhang et al., "DNA Polymorphisms in Strains of *Mycobacterium tuberculosis* Analyzed by Pulsed-Field Gel Electrophoresis: a Tool for Epidemiology", *J. of Clinical Micro.*, 30(6):1551–1556 (June 1992).
4. Gerald H. Mazurek et al., "Large DNA Restriction Fragment Polymorphism in the *Mycobacterium avium*-M intracellular Complex: a Potential Epidemiologic Tool", *J. of Clinical Micro.*, 31(2):390–394 (Feb. 1993).
5. Robert D. Arbeit et al., "Resolution of Recent Evolutionary Divergence among *Escherichia coli* from Related Lineages: The Application of Pulsed Field Electrophoresis to Molecular Epidemiology", *J. of Infectious Diseases*, 151:230–235 (1990).
6. Bruce Birren et al., *Pulsed Field Gel Electrophoresis: A Practical Guide*, Academic Press, Inc., (1993).

What is claimed is:

1. An apparatus for casting and processing a cell-containing agarose plug comprising:
   a mold forming a chamber dimensioned to form an agarose plug, said mold having a filling port allowing the filling of the chamber with molten agarose, said mold including two opposing sides;
   an opening in said mold through which solutions necessary to prepare DNA can access solidified agarose plugs within the mold chamber;
   at least one retainer for preventing molten agarose from exiting the mold through said opening, wherein the at least one retainer is placed through at least one slit in one of the opposing sides of the mold through the chamber and into at least one slit in the other of said opposing sides; and
   wherein the at least one retainer is positioned to block the opening during the pouring of molten agarose, thereby allowing the agarose to fill the chamber.

2. The apparatus of claim 1, wherein the mold comprises two halves connected together.

3. The apparatus of claim 2, wherein the two halves are substantially identical halves.

4. The apparatus of claim 2, wherein the two halves are connected by a connector projection/connector projection receiving hole system formed in each of the two halves.

5. The apparatus of claim 1, wherein the at least one retainer is at least one sheet retainer.

6. The apparatus of claim 5, wherein the at least one sheet retainer is plastic.

7. The apparatus of claim 5, wherein said at least one retainer comprises at least two sheet retainers defining a molding space within said chamber.

8. The apparatus of the claim 5, wherein the at least one sheet retainer is removable after agarose placed in the apparatus has solidified.

9. The apparatus of claim 1, wherein the opening comprises a plurality of holes.

10. A processing apparatus comprising a plug mold and at least one retainer, said plug mold having two halves, each half including a panel, two opposing sides extending from the panel, and an end extending from the panel, each panel having an opening for the passage of processing fluids into and out of a chamber defined by panels, sides and ends of the two halves, each half having a slot in each of the sides for receiving said at least one retainer, said at least one aid retainer passing through the slot on one opposing side through the chamber and into the slot in the other of said opposing sides for preventing molten agarose from flowing out of the chamber through said opening, the end of one half having a filling port for filling the mold with molten agarose, the two halves being joined together by a connector.

11. A method of obtaining DNA from cells comprising:
   providing an apparatus for casting and processing a cell containing agarose plug, wherein said apparatus comprises:
- a mold forming a chamber dimensioned to form an agarose plug, said mold having a filling port allowing the filling of the chamber with molten agarose;
- an opening in said mold through which solutions necessary to obtain the DNA can access solidified agarose plugs within the mold chamber; and
- at least one retainer covering said opening for preventing molten agarose from exiting the mold through said opening;

obtaining cells;

mixing the cells with molten agarose to form a molten agarose/cell mixture;

introducing the molten agarose/cell mixture into the apparatus through said filling port;

allowing the molten agarose to solidify to form agarose/cell plugs, removing the at least one retainer from the mold; and processing the agarose/cell plugs, while the plugs are contained within the mold, by exposing said plugs, through said opening, to suitable DNA preparation solutions under conditions and for a time suitable to obtain DNA.

12. A method of obtaining DNA from cells comprising:

providing a processing apparatus comprising a plug mold and at least one retainer, said plug mold having two halves, each half including a panel, two opposing sides extending from the panel, and an end extending from the panel, each panel having an opening for the passage of processing fluids into and out of a chamber defined by the panels, sides and ends of the two halves, each half having a slot in each of the sides for receiving said at least one retainer, said at least one retainer passing through the slot of one opposing side through the chamber and into the slot of the other of said opposing sides for preventing molten agarose from flowing out of the chamber through said opening, the end of one half having a filling port for filling the mold with molten agarose, the two halves being joined together by a connector;

inserting the at least one retainer through the slot of each half;

obtaining cells;

mixing the cells with molten agarose to form a molten agarose/cell mixture;

introducing the molten agarose/cell mixture into the apparatus through the filling port;

allowing the molten agarose to solidify to form agarose/cell plugs;

removing the at least one retainer from the mold; and processing the agarose/cell plugs, while the plugs are contained within the mold, by exposing said plugs, through said openings, to suitable DNA preparation solutions under conditions and for a time suitable to obtain the DNA.

* * * * *

UNITED STATES PATENT AND TRADEMARK OFFICE
CERTIFICATE OF CORRECTION

PATENT NO.    :    5,457,050

DATED         :    October 10, 1995

INVENTOR(S)   :    Gerald H. Mazurek

It is certified that error appears in the above-identified patent and that said Letters Patent is hereby corrected as shown below:

In claim 10, column 10, line 57, immediately after 'by' insert --the --.

In claim 10, column 10, line 59, delete "aid" and insert --said -- therefor.

Signed and Sealed this

Twenty-seventh Day of February, 1996

Attest:

BRUCE LEHMAN

*Attesting Officer*     *Commissioner of Patents and Trademarks*